(12) United States Patent
Samijo et al.

(10) Patent No.: US 9,999,514 B2
(45) Date of Patent: Jun. 19, 2018

(54) WRIST PROSTHESIS, AND A SET OF COMPONENTS FOR FORMING THE SAME

(71) Applicants: Stefano Kliwon Samijo, Gronsveld (NL); Rolandus Jacobus Josef Maria Oostwegel, Heerlen (NL)

(72) Inventors: Stefano Kliwon Samijo, Gronsveld (NL); Rolandus Jacobus Josef Maria Oostwegel, Heerlen (NL)

( * ) Notice: Subject to any disclaimer, the term of this patent is extended or adjusted under 35 U.S.C. 154(b) by 20 days.

(21) Appl. No.: 15/260,396

(22) PCT Filed: Mar. 12, 2015

(86) PCT No.: PCT/NL2015/050156
§ 371 (c)(1),
(2) Date: Sep. 9, 2016

(87) PCT Pub. No.: WO2015/137809
PCT Pub. Date: Sep. 17, 2015

(65) Prior Publication Data
US 2017/0151062 A1    Jun. 1, 2017

(30) Foreign Application Priority Data

Mar. 12, 2014  (NL) ..................................... 2012413

(51) Int. Cl.
*A61F 2/42* (2006.01)
*A61F 2/30* (2006.01)
(52) U.S. Cl.
CPC .. *A61F 2/4261* (2013.01); *A61F 2002/30253* (2013.01); *A61F 2002/30285* (2013.01);
(Continued)

(58) Field of Classification Search
CPC ..................................................... A61F 2/4261
See application file for complete search history.

(56) References Cited

U.S. PATENT DOCUMENTS

| 4,040,130 A | 8/1977 | Laure |
| 5,314,485 A | 5/1994 | Judet |

(Continued)

FOREIGN PATENT DOCUMENTS

| EP | 2 460 492 A1 | 6/2012 |
| FR | 2 661 817 A1 | 11/1991 |

(Continued)

OTHER PUBLICATIONS

Search Report for PCT/NL2015/050156.

*Primary Examiner* — Jason-Dennis Stewart
(74) *Attorney, Agent, or Firm* — Roberts & Roberts, LLP

(57) ABSTRACT

The invention relates to a wrist prosthesis (1), comprising a proximal prosthesis body (21) and a distal prosthesis body (11), wherein, at least in a deployed state of the wrist prosthesis, a portion of the proximal prosthesis body that faces away from the distal prosthesis body is provided with a convexly curved surface (22). Additionally, a portion of the distal prosthesis body that faces away from the proximal prosthesis body is furthermore provided with a convexly curved surface (12). Furthermore, the surfaces of the proximal prosthesis body and the distal prosthesis body that are facing each other are provided with complementary convex-concave curved surfaces (13, 23). The invention further relates to a set of components for such a wrist prosthesis, which allows the wrist prosthesis to be placed in a wrist, without anchoring means, and with a high degree of adaptation to the specific situation.

20 Claims, 2 Drawing Sheets

Figure 1A:
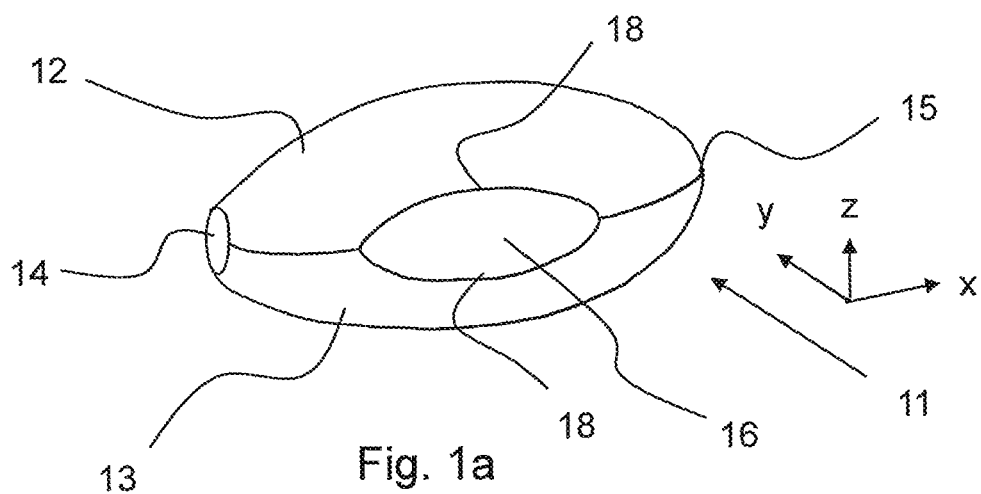

(52) U.S. Cl.
CPC ........... *A61F 2002/30528* (2013.01); *A61F 2002/4264* (2013.01); *A61F 2002/4274* (2013.01); *A61F 2002/4287* (2013.01); *A61F 2310/00143* (2013.01); *A61F 2310/00149* (2013.01)

(56) References Cited

U.S. PATENT DOCUMENTS

2004/0138754 A1  7/2004  Lang et al.
2007/0287027 A1  12/2007  Justin et al.

FOREIGN PATENT DOCUMENTS

FR      0 532 440 A1    3/1993
WO      2008/097781 A1  8/2008

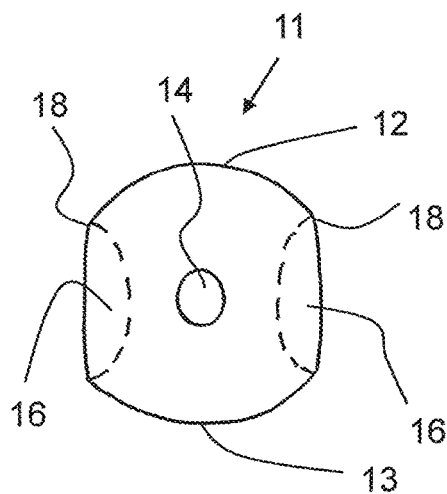
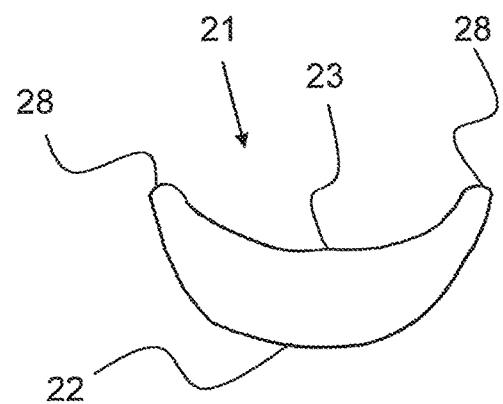
Fig. 2a          Fig. 2b
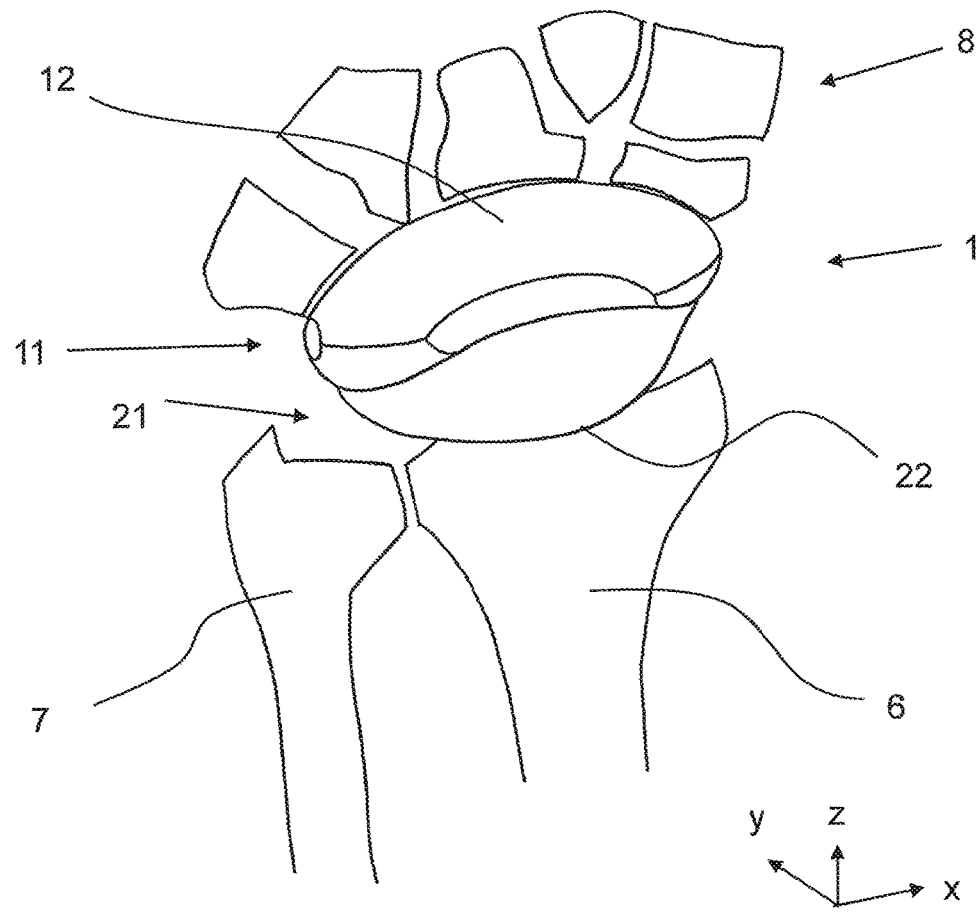
Fig. 3

WRIST PROSTHESIS, AND A SET OF COMPONENTS FOR FORMING THE SAME

The invention relates to a wrist prosthesis, as well as a set of parts for forming of a wrist prosthesis.

For example, a wrist prosthesis is known from EP 2 460 492 A1. Other prostheses are known from U.S. Pat. No. 4,040,130 A1, FR 2661817 A1, EP 0532440, and WO 2008/097781 A1.

The wrist prosthesis known from EP 2 460 492 A1 comprises a radiar component, and a carpal component. The radiar component is provided with anchoring means, by which the radiar component is anchorable in the radius. In order to provide an improved function on the carrier of the wrist prosthesis, the well known wrist prosthesis includes an intermediate component, which can be placed between the radiar component and the carpal component.

The disadvantage of the known wrist prosthesis is that it is subject to loosening and wear and tear, and therefore provides a reduced and painful movement. It is also a further drawback of the known wrist prosthesis, that the degree of mobility still exhibits a high degree of restrictions in function.

It is therefore an object of the present invention to provide a wrist prosthesis that reduces or alleviates at least one of the disadvantages of the known wrist prostheses. In particular, it is an object of the present invention to provide a wrist prosthesis, with a greatly reduced risk of wear and tear, and with an improved functionality.

To this end, the present invention provides a wrist prosthesis, comprising a prosthesis body proximal and a distal prosthesis body, wherein, at least in a deployed state of the wrist prosthesis:
  a portion of the proximal prosthesis body that faces away from the distal prosthesis body is provided with a convexly curved surface;
  a portion of the distal prosthesis body that faces away from the proximal prosthesis body is provided with a convexly curved surface;
  the surfaces of the proximal prosthesis body and the distal prosthesis body that are facing each other are provided with complementary convex-concave curved surfaces; and
  the wrist prosthesis is free of anchoring means.

The wrist prosthesis according to the invention comprises two parts, namely the proximal prosthesis body and the distal prosthesis body. The proximal prosthesis body, or the radiar component of the wrist prosthesis, can be placed on the distal prosthesis body, or the carpal component. In addition, the surfaces facing each other are designed to be complementary, in such a way that one of the surfaces is substantially of convex design, and the other one of the surfaces of concave design. As a result, relative movement between the proximal and distal prosthesis bodies is possible.

In the proximal prosthesis body of the prosthesis according to the present invention, the surface that faces away from the distal prosthesis body, that is to say that portion of the proximal prosthesis body that faces the radius in a deployed state, is designed to be convex, and in such a way that in a deployed state of the wrist prosthesis relative movement between the proximal prosthesis body and the radius of the person is possible. In contrast to the known state of the art, there is no fixation of the proximal prosthesis body to the radius, that is to say that the prosthesis is free of anchoring means, such that upon placement of the prosthesis no or only relatively little bone needs to be removed. Wear of the radius is minimized and loosening does not take place anymore.

In addition, the movable design, i.e. the non-fixed design, of the proximal prosthesis body relative to the radius, and together with the distal prosthesis body, ensures an improved degree of movement of the wrist prosthesis, which follows the movements of the wrist more faithfully.

In the distal prosthesis body of the prosthesis according to the present invention, the surface that faces away from the surface of the proximal prosthesis body, that is to say that portion of the distal prosthesis body that faces the carpal portion of the hand in a deployed state, is convex. By designing this part to be convex, and by using the two prosthesis bodies, a desired tension in the wrist joint may be provided, by a suitable choice of the dimensions of the individual prosthesis bodies, such that both flexion and extension, and radio deviation and ulnar deviation of the wrist joint is possible, whilst sufficient muscular tension is built up for the wrist and fingers. Partly due to the fact that there is no fixation of the prosthesis bodies, it can be experienced easily and quickly during placement of the prosthesis whether the proper tension has been reached, and if necessary, a prosthesis body may be replaced by a somewhat larger or smaller one.

With this, the wrist prosthesis according to the present invention provides for a wrist prosthesis with little to no wear and an optimal function, with which the goal according to the present invention is achieved.

Advantageous embodiments of the wrist prosthesis of the present invention are next explained in more detail.

The convexly curved surface of the proximal prosthesis body is, in an embodiment, at least in a deployed state, directed towards the radius of the person, and is movably in contact therewith. The convex curvature is arranged so that it forms an abutment, but also gives the proper radius for the wrist. The convexity of the proximal prosthesis body comprises the maximum radius as possible in the front-rear direction.

In one embodiment, the proximal body and the distal graft prosthesis body form loose parts, at least in a non-deployed state. This creates an enhanced relative motion between the prosthesis bodies, the component parts are simple to manufacture, and it is possible to select a suitable combination of two prosthetic bodies depending on the patient.

In one embodiment, no additional parts are needed, such that the prosthesis consists only of the proximal prosthesis body and the distal prosthesis body.

As already mentioned above, the proximal prosthesis body is located in a distal portion of the radius and the distal prosthesis body is located in the carpal portion in a deployed state of the wrist prosthesis.

In a preferred embodiment, the wrist prosthesis is provided with abutment means for limiting a relative movement between the proximal prosthesis body and the distal prosthesis body.

The abutment means are preferably adapted to limit flexion and dorsiflexion of the wrist in order to prevent luxation—when the prosthesis moves out of position, and out of the joint.

In a simple embodiment, the abutment means may be formed in that the proximal prosthesis body and the distal prosthesis body comprise a projection and a recess. The projection and the recess are complementary shaped such that relative movement is possible, but is limited, in that the recess forms an abutment for the projection.

It is preferred when the surfaces, that are designed to be complementary convex-concave, and that face each other are designed as follows: The surface of the proximal prosthesis body that faces the distal prosthesis body is designed to be convex, and the surface of the distal prosthesis body that faces the proximal prosthesis body is designed to be complementary concave.

An embodiment of the wrist prosthesis is characterized in that the proximal prosthesis body has substantially the same dimensions, but is slightly smaller than the distal prosthesis body. Examples will be dealt with later in the description of the figures.

In an embodiment of the wrist prosthesis, at least one of the proximal and distal prosthesis body is manufactured from a material comprising platinum/iridium. Such a material is wear-resistant, and does not oxidize, so the risk of metal intoxication is minimized.

At least one of the proximal or distal prosthesis body is provided with a layer of platinum, preferably rolled platinum. Preferably, the complementary convex-concave surfaces are provided with such a layer. Preferably, this layer is also polished smooth in a maximum manner, in order to have minimum friction. In addition, it is particularly preferred for all the surfaces of the prosthesis body in which motion and/or friction occurs, to be provided with a layer of platinum, such as rolled platinum, preferably polished smooth in a maximum manner.

The wrist prosthesis of the present invention is, as already mentioned, free of anchoring means. Advantages of such embodiment have already been explained above.

According to one aspect, the invention provides a set of parts for forming of a wrist prosthesis of the present invention. The set can comprise a proximal prosthesis body and a distal prosthesis body, as already described above.

In a possible embodiment, the set of components includes a proximal prosthesis body and a distal prosthesis body, wherein the proximal prosthesis body is provided with a convexly curved surface, wherein the distal prosthesis body is provided with a convexly curved surface, and wherein a surface that faces away from the convexly curved surface of the proximal prosthesis body, along with a surface that faces away from the convexly curved surface of the distal prosthesis body, form complementary convex-concave surfaces, in such a way that the proximal prosthesis body is movably positionable on the distal prosthesis body.

The set of parts also comprises a further proximal and/or further distal prosthesis body, which has been carried out in accordance with said proximal and/or said distal prosthesis body, wherein the further proximal and/or distal prosthesis body is larger than the proximal and/or distal prosthesis body.

Figure 1B:
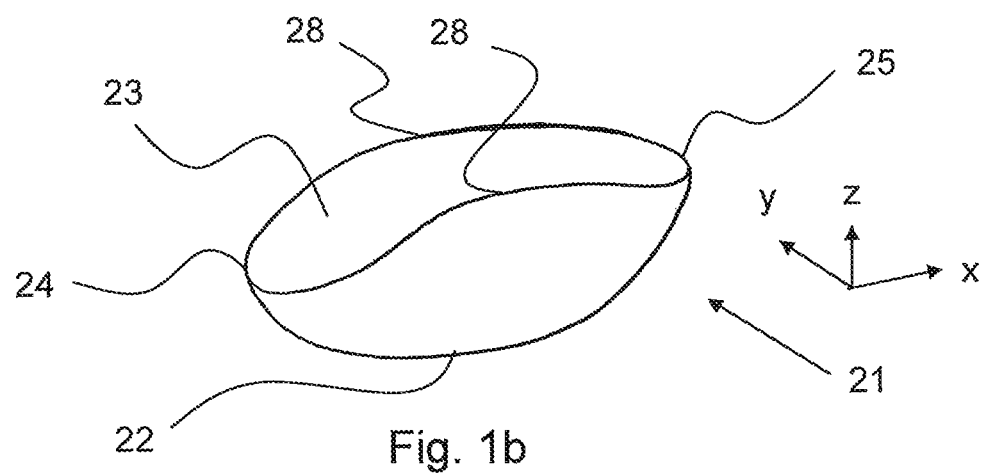
Figure 1C:
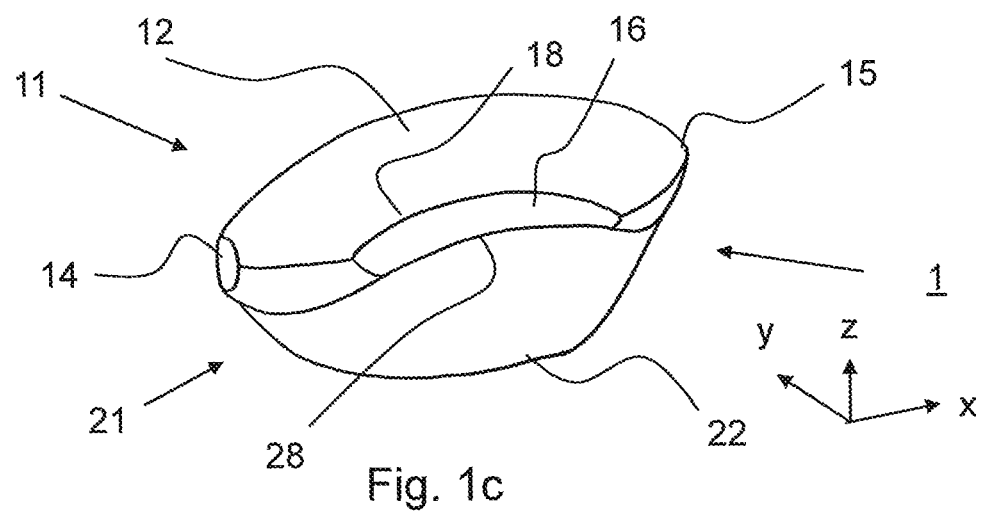

The invention will be further elucidated with reference to a preferred embodiment of the wrist prosthesis of the present invention, with reference to the attached Figures, in which:

FIG. 1a—is a perspective view of a prosthesis body of a wrist prosthesis according to the present invention;

FIG. 1b—is a perspective view of a prosthesis body of a wrist prosthesis according to the present invention;

FIG. 1c—shows a perspective view of a wrist prosthesis according to the present invention, composed of the prosthetic bodies of FIGS. 1a and 1b.

FIG. 2a—is a side view of the prosthesis body from FIG. 1a;

FIG. 2b—is a side view of the prosthesis body from FIG. 1b;

FIG. 3—a schematic view of the wrist prosthesis in a deployed state.

FIG. 1a shows a prosthesis body 11 for a wrist prosthesis 1 according to the present invention. In the embodiment shown, this prosthesis body 11 is a distal prosthesis body 11, that is to say that it is suitable to be placed distally, i.e., in a carpal portion of the wrist, as will be explained later with reference to FIG. 3.

Referring again to FIG. 1a, it can be seen that the distal prosthesis body 11 is generally egg-shaped, here more specifically in the shape of a rugby ball type. The prosthesis body 11 includes an upper surface 12 that is made convex. The upper surface is convexly curved between two end faces 14, 15 of the prosthesis body 11 (x-direction), but also convexly curved in a direction transverse to the first direction (y-direction). Thus a double-convex curved surface 12 is obtained. The distal prosthesis body 11 further also comprises a convexly curved surface 13 at a bottom surface 13 thereof, i.e. at the surface remote from the upper surface 12. This convexly curved surface 13 is also a double-convex curved surface, that is to say with a curvature in the direction of the first end face 14 to the second end face 15, but also with a curvature transversely to the line between the outer ends 14, 15.

FIG. 1b shows a prosthesis body 21, which together with the prosthesis body 11 of FIG. 1a forms a wrist prosthesis 1. This second prosthetic body 21 is, in the embodiment shown, a proximal prosthesis body 21, that is to say that it is suitable to be placed proximally, that is to say close to the radius. This proximal prosthesis body 21 is designed to be nest-shaped (see FIG. 2b), that is to say that a lower surface 22 is made convex, and that an upper surface 23 is made concave, and in such a way that a kind of receiving space 23 is formed in the prosthesis body 21. The convex surface 22 is double-convex, that is to say with a curvature in the x-direction and in the y-direction. The concave surface 23 has been designed to be double-concave, that is to say with a curvature in the x-direction and in the y-direction.

The concave surface 23 of the proximal prosthesis body 21, and the convex surface 13 of the distal prosthesis body 11, is designed such that these are complementary to each other, such that the distal prosthesis body 11 can be taken up by the proximal prosthesis body 21, for forming a wrist prosthesis 1 according to the present invention. This incorporated state is shown in FIG. 1c. Here it can be seen that a good connection is obtained between the prosthesis bodies 11, 21.

The two prosthetic bodies 11, 21 are, in the state shown in FIG. 1c, movable relative to each other, due to the fact that the complementary convex-concave surfaces can slide over each other. This results in a possible relative pivotal movement about the x-axis, as well as a possible relative pivotal movement about the y-axis. A relative pivotal movement about the z-axis, however, is counteracted. However, a pivotal movement about the z-axis is possible, since the proximal prosthesis body is movable with respect to the radius. As a result, an enhanced functionality compared to the known wrist prosthesis is obtained.

As can be seen in FIG. 1a, a recess 16 is provided in the distal prosthesis body. The recess is of concave design, and includes an edge 18 with the upper surface. This edge 18 forms an abutment for a projection 28 provided on the proximal prosthesis body, which projection is formed by the transition between the convex surface 22 and the concave surface 23 of the proximal prosthesis body 21. The recess and the projection form abutment means, which ensure that during a relative pivoting movement of the prosthetic bodies 21, 11, about the x-axis, the projection abuts onto or below the edge 18 of the recess. Thus, the relative movement about the x-axis is limited in order to avoid a dislocation of the two prosthetic bodies.

FIG. 2a shows a side view of the distal prosthesis body, wherein, in particular, the curvature of the upper surface 12 and the lower surface 13 and the concave curvature of the abutment means 16, are shown. In the embodiment shown, the distal prosthesis body 11 is made substantially symmetrical, with the upper surface 12 being substantially in the same form as the bottom surface 13. However, this is not necessary. Depending on the situation, adjustments can be made to the convex shapes.

FIG. 3, finally, shows an overview of a portion of the carpal bones of the wrist of a person, with a wrist prosthesis 1 according to the present invention therein. In the example shown, the distal prosthesis body and the proximal prosthesis body, as already described with reference to FIG. 1c, are placed in the body. The distal surface 12 of the distal prosthesis body is thereby directed to the carpal portion 8 of the wrist, and is in contact therewith. The proximal surface 22 of the proximal prosthesis body 21 is facing the radius 6, and is in contact therewith. The relative placement with respect to the ulna 7 can be seen here as well.

Thanks to the prosthesis of the present invention, a relative rotation of the prosthesis bodies about the x-axis is possible, which is associated with pronation and supination of the wrist joint. Furthermore, a relative rotation about the y-axis is possible as well, which is associated with radial and ulnar deviation of the wrist.

Advantageous of the wrist prosthesis of the present invention is that by suitable choice of the dimensions of the various prosthesis bodies, a suitable tissue tension can be achieved, such that the forces of the hand and the wrist are guaranteed. In particular, the proximal prosthesis body 21 is available in different heights (ranging in z-direction, see FIG. 1b), so that more or less capsular tension in the wrist can be obtained.

The invention is explained in more detail above with reference to a few embodiments. However, the invention is not limited to these embodiments. Many modifications are conceivable within the scope of the invention.

For example, it is conceivable that the proximal prosthesis body is provided with two convexly curved surfaces, and that the distal prosthesis body proper is provided with a convexly curved surface and a concavely curved surface. In other words, it is conceivable, that the prosthesis 1 as shown in FIG. 3, is placed the other way round, with the nest-shaped prosthesis body 21 near the carpal portion 8, and the egg-shaped prosthesis body 11 close to the radius.

The protection sought is defined by the appended claims.

The invention claimed is:

1. A wrist prosthesis comprising a proximal prosthesis body and a distal prosthesis body, wherein, at least in a deployed state of the wrist prosthesis:
   a portion of the proximal prosthesis body that faces away from the distal prosthesis body is provided with a convexly curved surface;
   a portion of the distal prosthesis body that faces away from the proximal prosthesis body is provided with a convexly curved surface;
   the surfaces of the proximal prosthesis body and the distal prosthesis body that are facing each other are provided with complementary convex-concave curved surfaces, wherein one of the distal prosthesis body and the proximal prosthesis body has a convexly curved surface and the other has a complementary concavely curved surface, such that the distal prosthesis body and the proximal prosthesis body are capable of being connected in such a way that they are slidably movable relative to each other; and
   the wrist prosthesis is free of anchoring means.

2. The wrist prosthesis according to claim 1, wherein the proximal prosthesis body and the distal prosthesis body, at least in a non-deployed state, form loose parts.

3. The wrist prosthesis according to claim 2 wherein in an installed condition of the wrist prosthesis the proximal prosthesis body is located in a distal portion of the radius, and wherein the distal prosthesis body is located in the carpal portion.

4. The wrist prosthesis according to claim 2 wherein the wrist prosthesis is provided with abutment means for restricting a relative movement between the proximal prosthesis body and the distal prosthesis body.

5. The wrist prosthesis according to claim 2, wherein the wrist prosthesis consists only of the proximal prosthesis body and the distal prosthesis body.

6. The wrist prosthesis according to claim 5 wherein in an installed condition of the wrist prosthesis the proximal prosthesis body is located in a distal portion of the radius, and wherein the distal prosthesis body is located in the carpal portion.

7. The wrist prosthesis according to claim 5 wherein the wrist prosthesis is provided with abutment means for restricting a relative movement between the proximal prosthesis body and the distal prosthesis body.

8. The wrist prosthesis according to claim 1, wherein the wrist prosthesis consists only of the proximal prosthesis body and the distal prosthesis body.

9. The wrist prosthesis according to claim 8 wherein in an installed condition of the wrist prosthesis the proximal prosthesis body is located in a distal portion of the radius, and wherein the distal prosthesis body is located in the carpal portion.

10. The wrist prosthesis according to claim 8 wherein the wrist prosthesis is provided with abutment means for restricting a relative movement between the proximal prosthesis body and the distal prosthesis body.

11. The wrist prosthesis according to claim 1, wherein in an installed condition of the wrist prosthesis the proximal prosthesis body is located in a distal portion of the radius, and wherein the distal prosthesis body is located in the carpal portion.

12. The wrist prosthesis according to claim 1, wherein the wrist prosthesis is provided with abutment means for restricting a relative movement between the proximal prosthesis body and the distal prosthesis body.

13. The wrist prosthesis according to claim 12, wherein the abutment means restrict flexion and dorsiflexion of the wrist.

14. The wrist prosthesis according to claim 12, wherein the proximal prosthesis body and the distal prosthesis body comprise a projection and a recess, which form the abutment means.

15. The wrist prosthesis according to claim 1, wherein the surface of the proximal prosthesis body that faces the distal prosthesis body is formed convex, and wherein the surface of the distal prosthesis body that faces the proximal prosthesis body is formed complementary concave.

16. The wrist prosthesis according to claim 1, wherein the proximal prosthesis body is substantially smaller than the distal prosthesis body.

17. The wrist prosthesis according to claim 1, wherein at least one of the proximal and the distal prosthesis body is made of a material comprising platinum/iridium.

18. The wrist prosthesis according to claim 1, wherein at least one of the proximal and the distal prosthesis body is provided with a layer of rolled platinum.

19. A set of parts for forming of a wrist prosthesis according to claim 1, comprising a proximal prosthesis body and a distal prosthesis body, wherein the proximal prosthesis body is provided with a convex curved surface, wherein the distal prosthesis body is provided with a convex curved surface, and wherein a surface that faces away from the convex curved surface of the proximal prosthesis body, along with surface that faces away from the convex curved surface of the distal prosthesis body, form complementary convex-concave surfaces, in such a way that the proximal prosthesis body is movably positionable on the distal prosthesis body, and wherein the wrist prosthesis is free of anchoring means.

20. The set of parts according to claim 19, comprising a further proximal prosthesis body and/or a further distal prosthesis body, which has/have been designed in accordance with said proximal and/or said distal prosthesis body, wherein the further proximal prosthesis body and/or distal prosthesis body is larger than the proximal prosthesis body and/or distal prosthesis body.

* * * * *